United States Patent [19]

Perry

[11] Patent Number: 5,222,892
[45] Date of Patent: Jun. 29, 1993

[54] LABORATORY ATTACHMENT JIG FOR PROSTHODONTIC RESTORATION

[76] Inventor: William L. Perry, 1517 Live Oak, Irving, Tex. 75061

[21] Appl. No.: 870,146

[22] Filed: Apr. 17, 1992

[51] Int. Cl.⁵ .............................................. A61C 3/00
[52] U.S. Cl. ...................................... 433/75; 433/50
[58] Field of Search ...................... 433/75, 76, 49, 50

[56] References Cited

U.S. PATENT DOCUMENTS

| | | | |
|---|---|---|---|
| 1,447,774 | 3/1923 | Fortunati | 433/75 |
| 2,528,053 | 10/1950 | Harris | 433/75 |
| 3,344,525 | 10/1967 | Harris | 433/75 |
| 4,264,308 | 4/1981 | Tanaka | 433/223 |
| 4,758,159 | 7/1988 | Weissman | 433/161 |

FOREIGN PATENT DOCUMENTS 1457917 2/1989 U.S.S.R. .............. 433/49

*Primary Examiner*—Gene Mancene
*Assistant Examiner*—Cindy A. Cherichetti
*Attorney, Agent, or Firm*—David H. Judson

[57] ABSTRACT

A laboratory attachment jig is described for use in accurately positioning an attachment relative to an implant abutment/fixture analog of a working model. This jig comprises an orientation arm having a first end and a second end, the orientation arm including a fastener for securing the orientation arm to the abutment/fixture analog of the working model. A primary support member is attached to the second end of the orientation arm, with the primary support member and the orientation arm being supported transversely in a first plane. The primary support member includes a vertical positioning sleeve and a fastener for the vertical positioning sleeve. A lateral support arm is attached to the vertical positioning sleeve of the primary support member and includes an end. A mandrel support member is attached to the end of the lateral support member for retaining the attachment. The lateral support arm includes a lateral positioning sleeve and a fastener for the lateral positioning sleeve. In use, the lateral support arm is adapted to be movable up or down on the primary support member upon loosening of the fastener for the vertical positioning sleeve and is adapted to be movable forward or backward relative to the primary support member upon loosening of the fastener for the lateral positioning sleeve.

6 Claims, 5 Drawing Sheets

LABORATORY ATTACHMENT JIG FOR PROSTHODONTIC RESTORATION

TECHNICAL FIELD

The present invention relates generally to implant restorative dentistry and more particularly to a laboratory attachment jig for use during prosthodontic restoration to accurately position an attachment to an implant abutment/fixture analog located on a working model.

BACKGROUND OF THE INVENTION

When implants are used with natural teeth, attachments are usually indicated as stress breakers. At other times, it may also be advantageous to incorporate attachments into frameworks when restoring implants. Traditionally, a surveyor or similar tool is used to parallel and place attachments in a working model. Unfortunately, however, many technicians are uncomfortable with using a surveyor and thus cannot or do not achieve the optimal benefits thereof. Further, use of a surveyor requires significant precision and the process is often time-consuming and costly.

There is therefore a need for improved methods and devices for use in extra-oral placement and positioning of attachments in a dental restoration.

BRIEF SUMMARY OF THE INVENTION

It is an object of the present invention to provide a novel laboratory attachment jig for use during dental prosthodontic restoration.

It is a further object of the invention to use the laboratory attachment jig for paralleling an attachment to an implant abutment/fixture analog located on a working model.

It is still another object to provide a laboratory attachment jig that is simple to use and that reliably and accurately positions an attachment in a working model for use in a dental restoration.

It is yet another object to provide a method for using a laboratory attachment jig during a prosthodontic restoration that provides enhanced precision and reduced working time for the technician as compared to prior art surveyor techniques.

These and other objects of the invention are provided in a laboratory attachment jig for use in accurately positioning an attachment relative to an implant abutment/fixture analog of a working model. This jig comprises an orientation arm having a first end and a second end, the orientation arm including a fastener for securing the orientation arm to the abutment/fixture analog of the working model. A primary support member is attached to the second end of the orientation arm, with the primary support member and the orientation arm being supported transversely in a first plane. The primary support member includes a vertical positioning sleeve and a fastener for the vertical positioning sleeve. A lateral support arm is attached to the vertical positioning sleeve of the primary support member and includes an end. A mandrel support member is attached to the end of the lateral support member for retaining the attachment. The lateral support arm includes a lateral positioning sleeve and a fastener for the lateral positioning sleeve. In use, the lateral support arm is adapted to be movable up or down on the primary support member upon loosening of the fastener for the vertical positioning sleeve and is adapted to be movable forward or backward relative to the primary support member upon loosening of the fastener for the lateral positioning sleeve.

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention as will be described. Accordingly, other objects and a fuller understanding of the invention may be had by referring to the following Detailed Description of the preferred embodiment.

BRIEF DESCRIPTION OF THE DRAWINGS

For a more complete understanding of the present invention and the advantages thereof, reference should be made to the following Detailed Description taken in connection with the accompanying drawings in which.

Similar reference characters refer to similar parts throughout the several views of the drawings.

DETAILED DESCRIPTION

Figure 1:
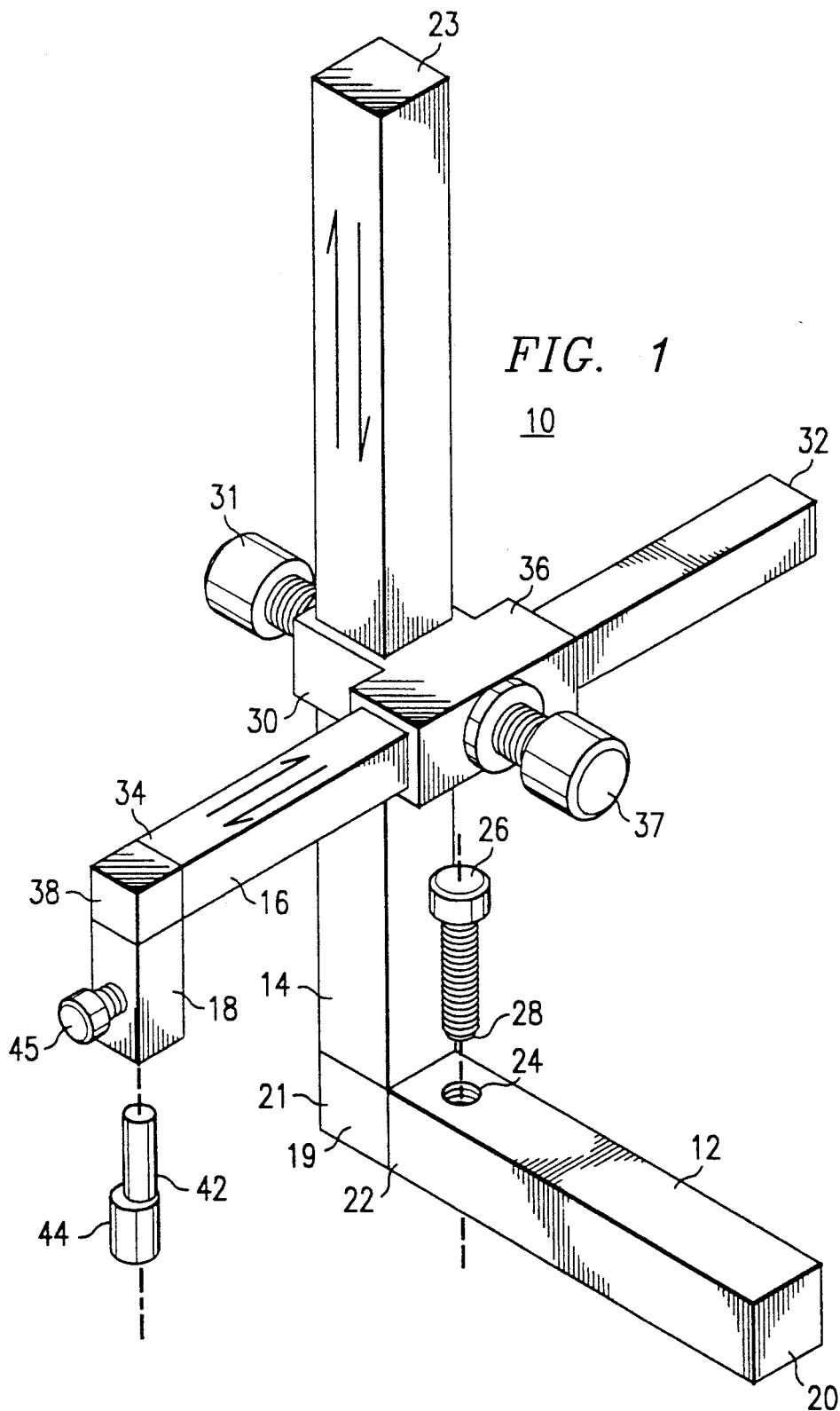
FIG. 1 is a perspective view of the laboratory attachment jig of the present invention.

Referring now to FIG. 1, the laboratory attachment jig 10 of the present invention comprises an orientation arm 12, a primary support member 14, a lateral support arm 16, and a mandrel support member 18. Each of these structural members are preferably formed of a rigid plastic or lightweight metal material. The orientation arm has a first end 20 and a second end 22. The primary support member 14 and includes a first end 21 and a second end 23. Primary support member 14 is mounted at its first end 21 tranversely to the second end 22 of the orientation arm 12 substantially as shown. Orientation arm 12 and primary support member 14 are thus located in the same plane. A threaded opening 24 adjacent the second end 22 of the orientation arm 12 receives an analog fastening screw 26. The end 28 of the analog fastening screw is adapted to be secured to an implant abutment fixture analog located on a working model as will be described below. A ball pivot joint 19 may be provided to enable the member 14 to pivot relative to the orientation arm 12 when the arm is in a fixed position. If the pivot joint 19 is used, a lock (not shown) is also provided to fix the position of the member 14.

The primary support member 14 is generally square-shaped in cross-section and includes a vertical positioning sleeve 30 and set screw 31. The lateral support arm 16 is attached to the vertical positioning sleeve 30 and thus is movable therewith. By loosening the set screw 31 (or other suitable fastener), the lateral support arm 16 is movable up and down on the primary support member 14 relative to the orientation arm 12. By tightening the set screw 31, the vertical position of the lateral support arm 16 is then fixed.

As seen in FIG. 1, the lateral support arm 16 is located in (and moves vertically in) a plane slightly offset from the vertical plane in which the primary support member is located. Lateral support arm includes a first end 32 and a second end 34, and a lateral positioning sleeve 36. A set screw 37 is supported in the positioning sleeve 36 and is loosened to enable the lateral support arm 16 to move laterally (i.e., forward and backward) relative to the primary support arm 14.

The laboratory attachment jig 10 also includes the mandrel support member 18 that is attached to the second end 34 of the lateral support arm 16 via a pivot joint 38. The mandrel support member 18 includes an internal bore in which is received an attachment mandrel 42. The attachment mandrel 42 includes the attachment 44 to be positioned. A mandrel set screw 45 is used to retain the attachment mandrel (with the attachment) in the mandrel support member. The pivot joint 38 enables the mandrel support member 18 to pivot approximately 15 degrees relative to the axis passing through the lateral support arm 16. A suitable lock (not shown) fixes the position of the pivotable member 18.

Figure 2:
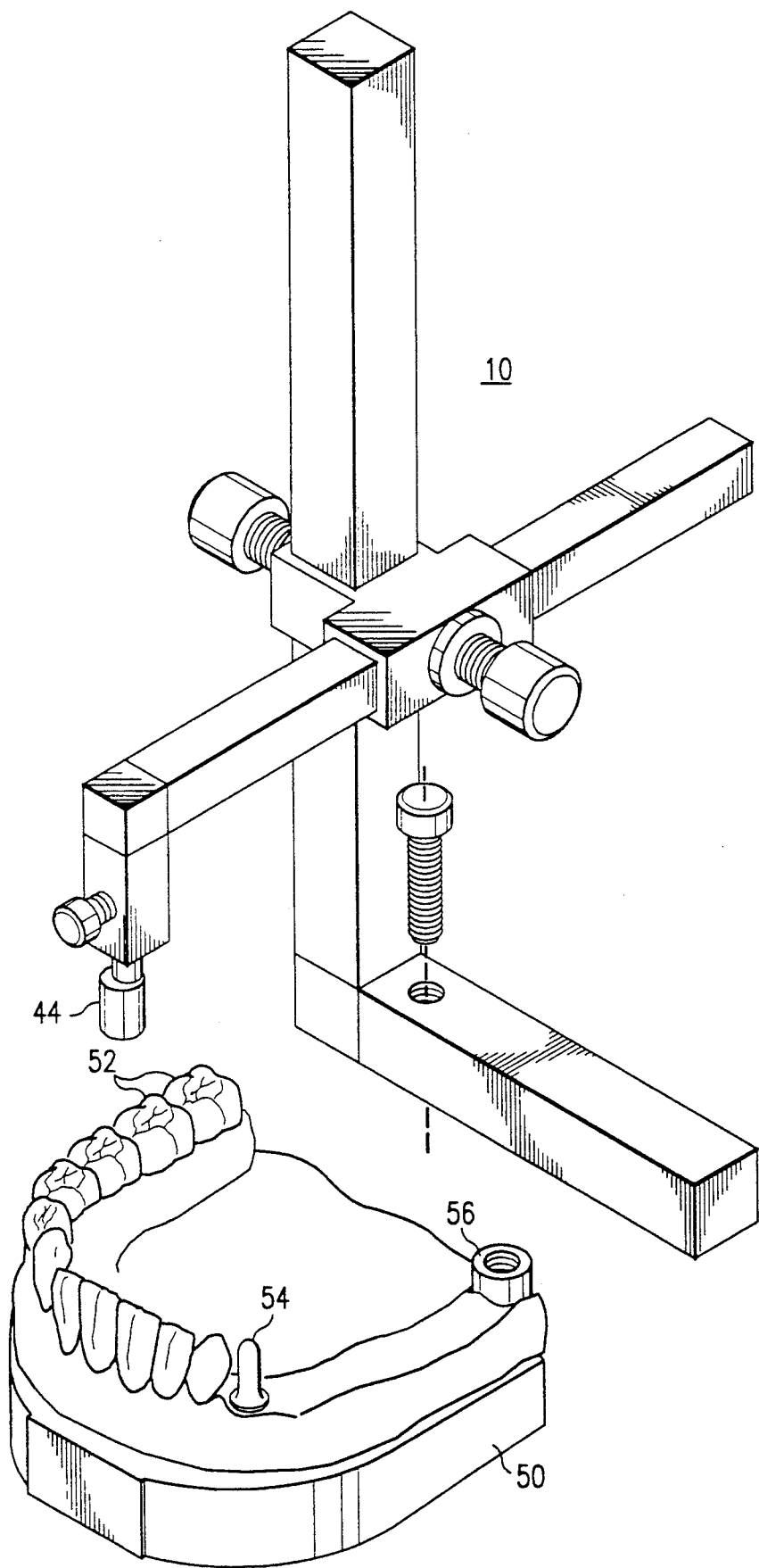
FIG. 2 is a perspective view of the laboratory attachment jig of FIG. 1 with an attachment mandrel secured therein, the jig being oriented over a working model according to a method of the present invention.

The use of the laboratory attachment jig 10 shown in FIG. 1 can now be described with reference to the method diagrammed in FIGS. 2-7. As seen in FIG. 2, the laboratory attachment jig is particularly adapted for use extra-orally in connection with a working cast model 50. The working model is a simulation of the patient's lower jaw (by way of example only) and includes a plurality of teeth 52 (representing the patient's natural teeth), at least one implant abutment 54, and an implant abutment/fixture analog 56. According to the method, it is desired to properly position the attachment 44 adjacent the implant abutment 54 (which represents the position of an osseointegrated dental implant in the patient's mouth) parallel to the implant abutment/fixture analog 56.

Figure 4:
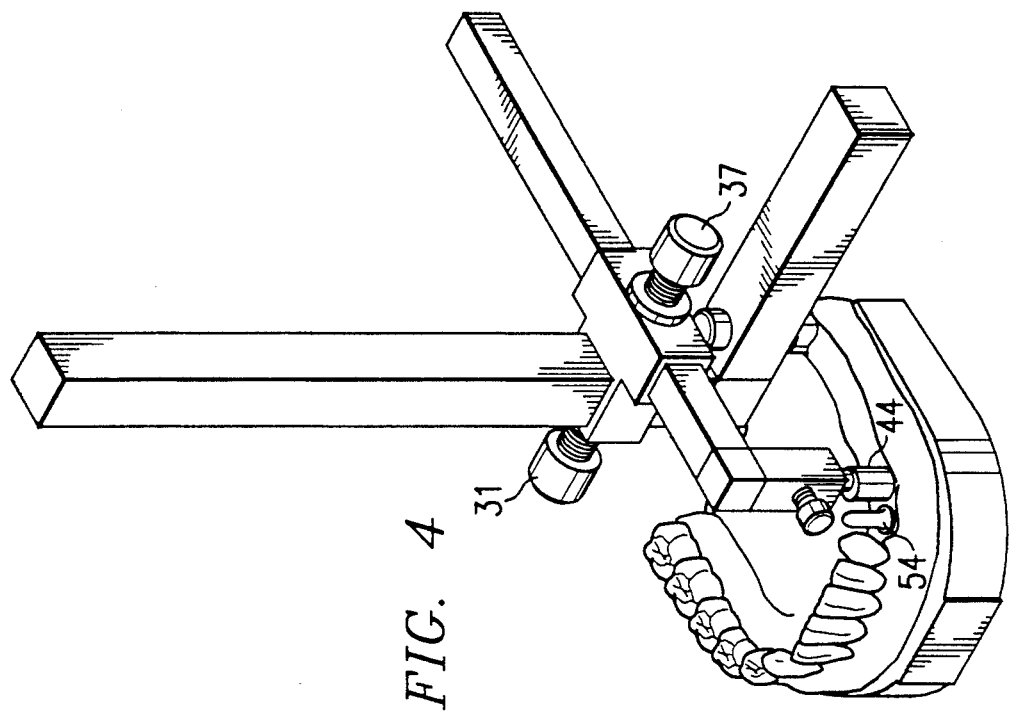
FIG. 4 is a perspective view of the laboratory attachment jig with the attachment positioned in the desired mesio-distal, occluso-cervical and bucco-lingual orientations according to the method of the invention.

Referring now specifically to FIG. 2, the method begins by securing the attachment mandrel 42 (with the attachment 44) to the mandrel support member 18 and generally positioning the jig over the cast model. The method continues in FIG. 3 with the technician securing the analog fastening screw 26 to the implant abutment/fixture analog 56. Referring now to FIG. 4, the attachment 44 is then positioned relative to the implant abutment 54 in the correct mesio-distal and occluso-cervical orientation by manipulating the lateral support arm 16 up or down relative to the primary support member. As noted above, this is accomplished by loosening the set screw 31. The attachment is placed in the correct bucco-lingual position by manipulating the lateral support arm forward or backward upon loosening the set screw 37. Once the positioning is complete, the set screws are tightened.

Figure 6:
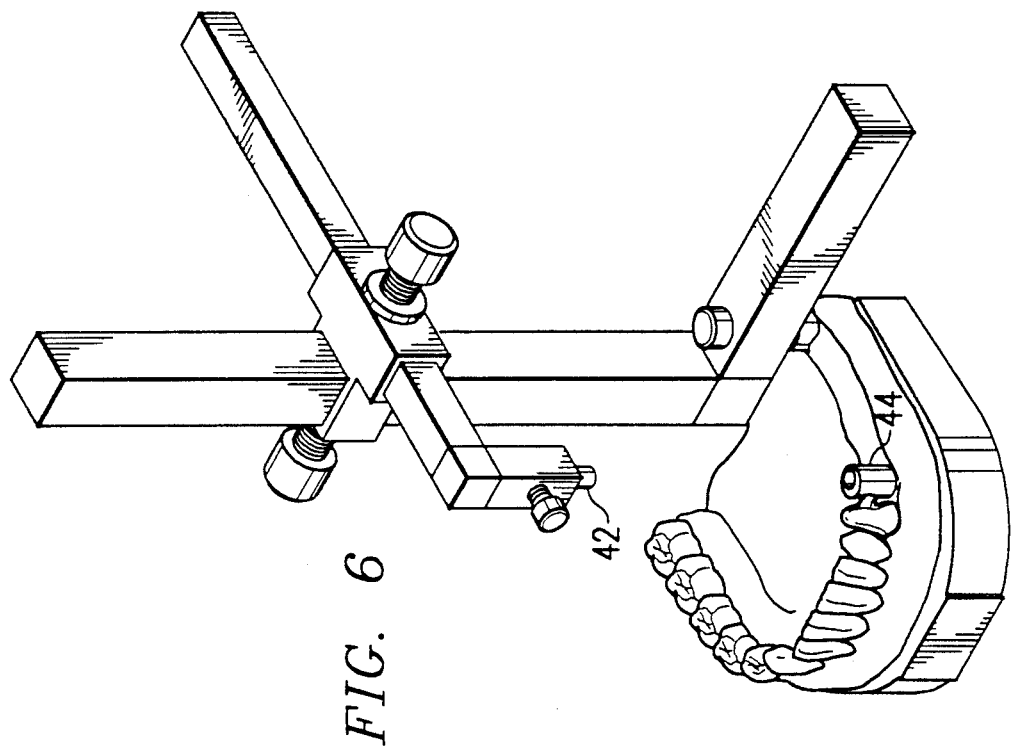
FIG. 6 is a perspective view of the laboratory attachment jig mandrel disconnected from the attachment according to the method of the present invention.
Figure 5:
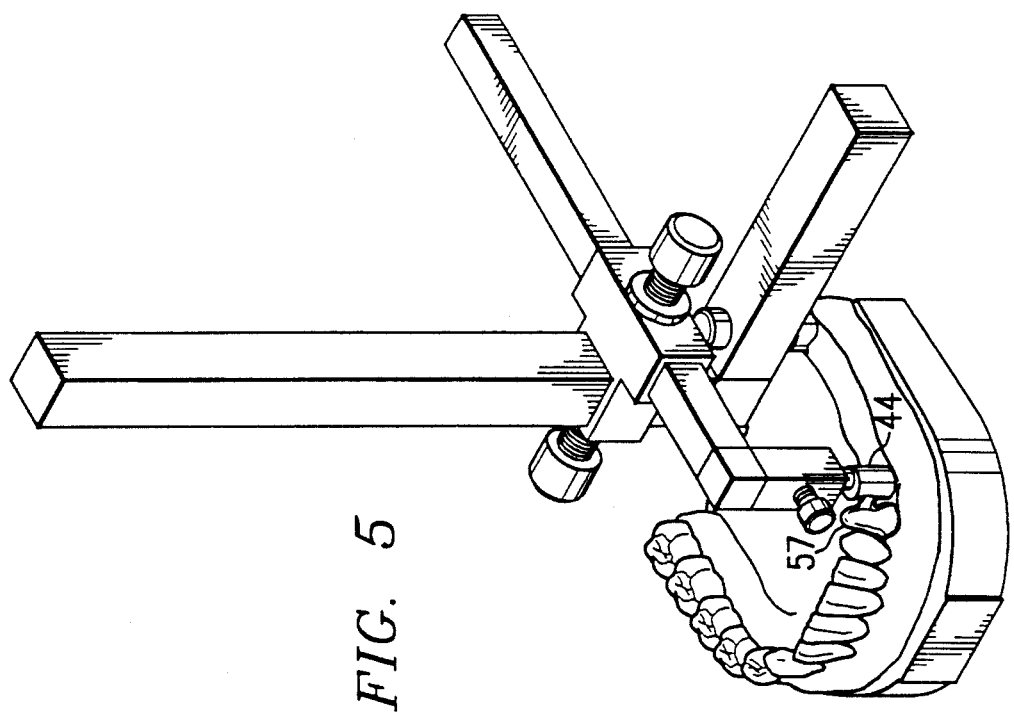
FIG. 5 is a perspective view showing the attachment being waxed to the abutment according to the inventive method.
Figure 8:
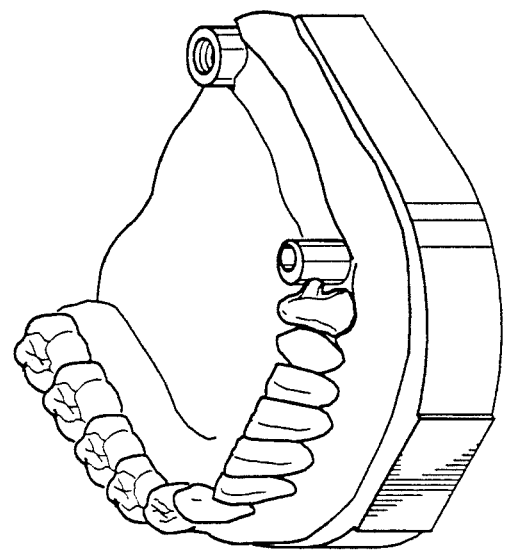
FIG. 8 is a perspective view of the completed working model.
Figure 7:
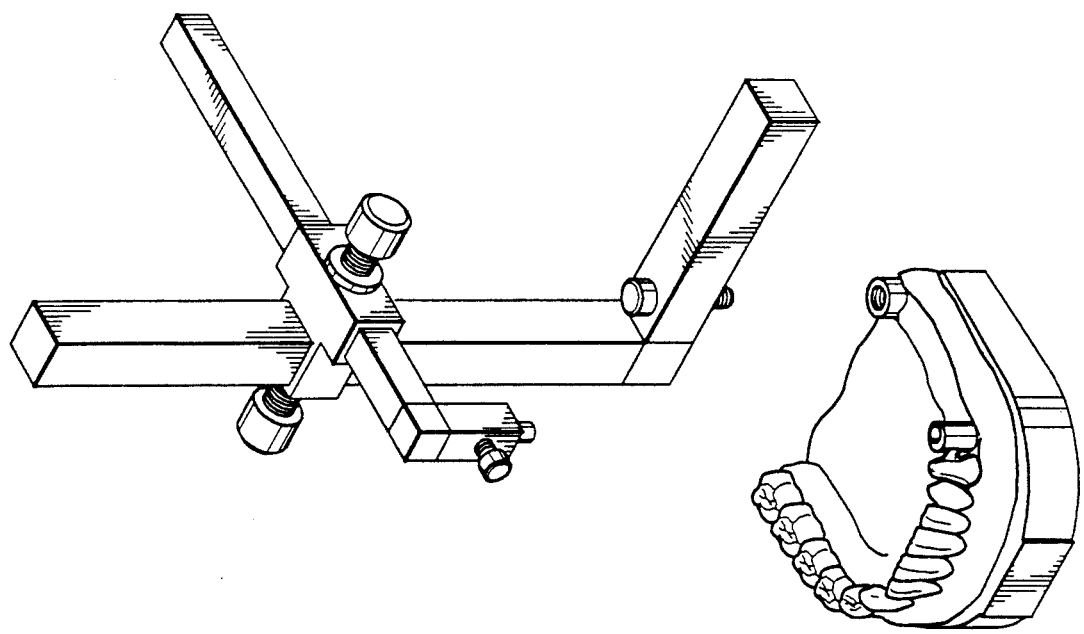
FIG. 7 is a perspective view of the laboratory attachment jig following its removal from the working model.

Referring now to FIG. 5, the method continues by waxing (with wax 57) the attachment 44 to the adjacent abutment 54. As seen in FIG. 6, the mandrel 42 is then separated from the attachment 44. At FIG. 7, the jig 10 is removed from the working model. The attachment 44 is now secured to the abutment 54, paralleled to the implant analog 56, and ready to be completed with standard prior art procedures. The completed working model is shown in FIG. 8.

As noted above, the jig 10 advantageously includes a 15° pivot joint between the second end of the lateral support arm and the mandrel support member. This enables the jig to be used as a surveying tool and to thus allow for fabrication without the attachment 44. For example, abutment 54 could support a coping, and a fixed bridge could then be drawn between the abutment and the analog 56.

Figure 3:
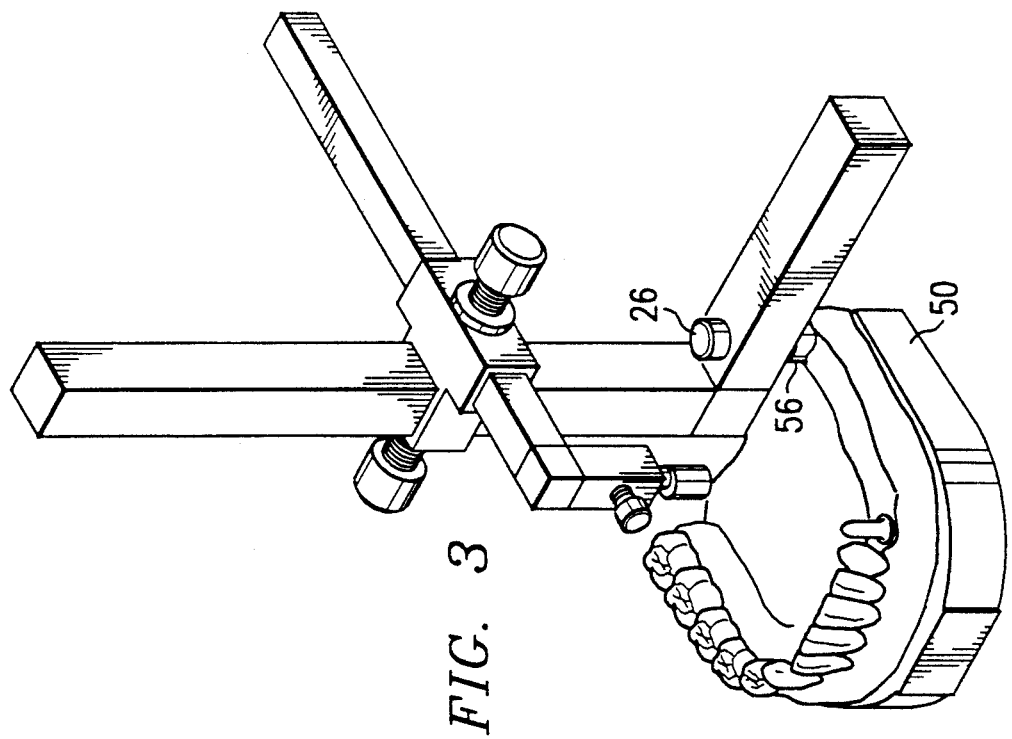
FIG. 3 is a perspective view of the laboratory attachment jig secured to an implant abutment/fixture analog on the working model according to the method of the invention.

In particular, the orientation arm 12 is first attached to the analog 56 as in FIG. 3. The mandrel support member 18 (and/or mandrel 42) is then oriented over the coping. Angular variations in the orientation of the coping are then taken into consideration by pivoting and adjusting members 14 and 18 (via ball joints 19 and 38). The coping is then waxed.

It should be appreciated by those skilled in the art that the specific embodiments disclosed above may be readily utilized as a basis for modifying or designing other structures for carrying out the same purposes of the present invention. It should also be realized by those skilled in the art that such equivalent constructions do not depart from the spirit and scope of the invention as set forth in the appended claims.

What is claimed is:

1. A laboratory attachment jig for use in accurately positioning an attachment relative to an implant abutment/fixture analog of a working model, comprising:

an orientation arm having a first end and a second end, the orientation arm adapted to overlay the abutment/fixture analog of the working model and including a fastener for securing the orientation arm to the abutment/fixture analog of the working model;

a primary support member attached to the second end of the orientation arm, with the primary support member and the orientation arm being supported transversely in a first plane;

the primary support member including a vertical positioning sleeve and a fastener for the vertical positioning sleeve;

a lateral support arm attached to the vertical positioning sleeve of the primary support member and including an end;

the lateral support arm including a lateral positioning sleeve and a fastener for the lateral positioning sleeve;

wherein the lateral support arm is adapted to be movable up or down on the primary support member upon loosening of the fastener for the vertical positioning sleeve and is adapted to be movable forward or backward relative to the primary support member upon loosening of the fastener for the lateral positioning sleeve; and a mandrel support member attached to the end of the lateral support member for retaining the attachment.

2. The laboratory attachment jig as described in claim 1 wherein the mandrel support member is attached to the end of the lateral support member through a pivot joint.

3. The laboratory attachment jig as described in claim 2 wherein the mandrel support member includes an internal bore in which is received an attachment mandrel, the attachment mandrel including the attachment at one end.

4. The laboratory attachment jig as described in claim 3 wherein the mandrel support member includes a fastener to retain the attachment mandrel with the attachment in the mandrel support member.

5. A laboratory attachment jig for use in accurately positioning an attachment relative to an implant abutment/fixture analog of a working model, comprising:

an orientation arm having a first end and a second end, the orientation arm including a fastener for securing the orientation arm to the abutment/fixture analog of the working model;

a primary support member attached to the second end of the orientation arm, with the primary support member and the orientation arm being supported transversely in a first plane;

the primary support member including a vertical positioning sleeve and a fastener for the vertical positioning sleeve;

a lateral support arm attached to the vertical positioning sleeve of the primary support member and including an end;

the lateral support arm including a lateral positioning sleeve and a fastener for the lateral positioning sleeve;

wherein the lateral support arm is adapted to be movable up or down on the primary support member upon loosening of the fastener for the vertical positioning sleeve and is adapted to be movable forward or backward relative to the primary support member upon loosening of the fastener for the lateral positioning sleeve; and a mandrel support member attached to the end of the lateral support member for retaining the attachment, wherein the mandrel support member includes an internal bore in which is received an attachment mandrel, the attachment mandrel including the attachment at one end.

6. The laboratory attachment jig as described in claim 5 wherein the mandrel support member includes a fastener to retain the attachment mandrel with the attachment in the mandrel support member.

* * * * *